United States Patent [19]

Jacobson et al.

[11] Patent Number: 5,595,750
[45] Date of Patent: *Jan. 21, 1997

[54] ANTIMICROBIAL PARTICLES OF SILVER AND BARIUM SULFATE OR ZINC OXIDE

[75] Inventors: Howard W. Jacobson; Michael H. Scholla; Annie W. Wigfall, all of Wilmington, Del.

[73] Assignee: E. I. Du Pont de Nemours and Company, Wilmington, Del.

[*] Notice: The term of this patent shall not extend beyond the expiration date of Pat. No. 5,180,585.

[21] Appl. No.: 361,003

[22] Filed: Dec. 21, 1994

Related U.S. Application Data

[63] Continuation of Ser. No. 6,022, Jan. 15, 1993, abandoned, which is a continuation of Ser. No. 742,963, Aug. 9, 1991, Pat. No. 5,180,585.

[51] Int. Cl.$^6$ .......................... A01N 25/26; A01N 59/16
[52] U.S. Cl. ......................... 424/421; 424/404; 424/405; 424/618
[58] Field of Search ........................ 424/404, 405, 424/408, 409, 485, 489, 618, 421, 411–415, 635, 641, 642, 76.9, 78.07; 428/403, 404, 407, 903, 556, 570; 523/210, 211, 216, 122, 576; 524/440, 430

[56] References Cited

U.S. PATENT DOCUMENTS

| | | | |
|---|---|---|---|
| 2,885,366 | 5/1959 | Iler | 252/313 |
| 3,649,321 | 3/1972 | Durant et al. | 106/300 |
| 3,785,798 | 1/1974 | Horai et al. | 71/79 |
| 4,464,317 | 8/1984 | Thies et al. | 264/4.3 |
| 5,047,448 | 9/1991 | Tanaka et al. | 523/122 |
| 5,064,599 | 11/1991 | Ando et al. | 264/237 |
| 5,122,418 | 6/1992 | Nakane et al. | 424/401 |
| 5,180,585 | 1/1993 | Jacobson et al. | 424/405 |

FOREIGN PATENT DOCUMENTS

| | | |
|---|---|---|
| 0253663 | 7/1986 | European Pat. Off. . |
| 0251783 | 1/1988 | European Pat. Off. . |
| 0427858 | 9/1990 | European Pat. Off. . |
| 0488269 | 6/1992 | European Pat. Off. . |
| 80106758 | 8/1991 | Taiwan . |
| 059193 | 2/1993 | Taiwan . |
| 9009736 | 9/1990 | WIPO . |

OTHER PUBLICATIONS

* Taiwanese counterpart to USPN 5,180,585.
Applicants hereby list the information cited by or submitted to the USPTO in the following prior U.S. patent applications for which an earlier filing date is relied upon under 35 U.S.C. Section 120: 1. S.N. 07/742,963, filed Aug. 9, 1991 (CH–2079), now U.S. Patent 5,180,585.

*Primary Examiner*—Neil S. Levy

[57] ABSTRACT

An antimicrobial composition comprising an inorganic particle with a first coating providing antimicrobial properties and a second coating providing a protective function is disclosed with a method for preparing the same and uses; further processes for producing polymeric articles and a method for controlling microorganisms are also disclosed.

12 Claims, No Drawings

ANTIMICROBIAL PARTICLES OF SILVER AND BARIUM SULFATE OR ZINC OXIDE

This is a continuation, of application Ser. No. 08/006,022 filed Jan. 15, 1993, now abandoned, which is a continuation of application Ser. No. 07/742,963, filed Aug. 9, 1991, U.S. Pat. No. 5,180,585.

BACKGROUND OF THE INVENTION

1. FIELD OF THE INVENTION

The invention is directed to an antimicrobial powder composition comprising inorganic particles having a primary surface coating of a metal or metal compound and a secondary coating providing a protective function such as silica and alumina or alumina, and processes for enhancing dispersibililty.

A further aspect of the invention is directed to a polymeric article comprising at least one polymer and the aforementioned antimicrobial composition, and processes for producing said polymeric article. The invention also is directed to bifunctional powders, which can be used to deluster fibers as well as to provide antimicrobial properties.

Another aspect of the invention is directed to a method for controlling microorganisms and various applications based on the use of the aforementioned antimicrobial materials.

2. DESCRIPTION OF THE RELATED ART

Polymeric articles having antimicrobial properties are described in the literature. Such articles are made in various shapes and dimensions such as granules, films, fibers, containers, pipes, structural components, medical appliances, etc. It is also known that certain metals such as silver, copper and zinc or their compounds are effective as antimicrobial agents. Numerous attempts have been made to utilize this attribute in polymeric articles.

For example, U.S. Pat. No. 4,906,466 describes an antimicrobial composition comprising a silver compound, selected from AgCl, AgBr, $Ag_2CO_3$ and $Ag_3PO_4$, deposited on a physiologically inert particle, selected from oxides of Ti, Mg, Al, Si, Ce, Hf, Nb and Ta, calcium hydroxyapatite and barium sulfate. It is disclosed that the compositions may be modified by the inclusion of other ingredients such as dispersion aids, and these compositions may be incorporated in polymeric materials in an amount of from 5–60% by weight of the composite. The antimicrobial silver compound in contact with the polymer article may interact with it producing undesired effects, such as darkening due to reduction to metallic silver.

Several patents describe antimicrobial compositions in which zeolite particles are supports for antimicrobial metal ions. Zeolites are aluminosilicates, of either natural or synthetic origin, which have sites at which cationic exchange may occur. By treating them with solutions of metal ions a desired antimicrobial metal ion can be substituted in the zeolite structure. Polymer articles having antimicrobial properties are made by incorporating the treated zeolites with the polymer or the zeolite can be mixed with the polymer and then treated with a solution of the desired antimicrobial metal ion. There are no barrier coatings on the particles to prevent interactions of the metal ions with the polymer, to control the rate of release of the antimicrobial species or to facilitate dispersion of the particles in the polymer article. For example, the use of the zeolite particles in polymer articles is described in detail in U.S. Pat. No. 4,775,585, and, more specifically, U.S. Pat. No. 4,525,410 is directed to fiber applications. Further, it is recognized that zeolite powders tend to agglomerate and are inferior in dispersibility when mixed with resins. U.S. Pat. No. 4,741,779 adds fine silica, dry or as a sol, to provide a zeolite powder which has high free-flowability and low agglomerating properties. Such problems as aggregation and color development in polymer antimicrobial zeolite compositions are also addressed in J 01164722 which relates to the use of additives such as fatty acid salts to aid dispersion and UV-light absorbers to prevent color development.

It is most desirable that the antimicrobial additive be easily dispersible within the polymer matrix without any significant adverse effects on polymer properties. It is also desirable that the antimicrobial be effective in controlling microorganisms at economic levels of use and remain active for months or years. Most commercially available compositions suffer from several deficiencies in the end use. They are often agglomerated and therefore difficult to disperse in end use systems. In addition, in the end use systems, the antimicrobial component is in direct contact with the product matrix with which it may react, leading to deterioration in properties, development of coloring or staining and other undesirable features. The development of color occurs during the shaping process, i.e., producing a shaped polymeric article. The cause for color deterioration may be attributed to the high metal loadings of the prior art. There is a need for antimicrobial compositions which do not have these deficiencies particularly when they are incorporated in a polymer matrix. The composition of the present invention meets this need.

SUMMARY OF THE INVENTION

One aspect of the invention relates to an antimicrobial composition comprising inorganic particles having a first coating, i.e., primary coating of a metal or metal compound, i.e., antimicrobial species or component of about 0.05 to 20% by weight of a core material. The first coating provides antimicrobial properties. A secondary coating comprises a layer of silica, silicates, borosilicates, aluminosilicates, alumina or mixtures thereof of about 0.5 to 20% by weight of the core material. The secondary coating functions as a barrier between the antimicrobial particle and a polymer matrix in which it may be incorporated, minimizing interaction with the polymer. In the absence of such a barrier adverse interactions can occur between the polymer matrix and the antimicrobial component. This may result in undesirable coloring or staining of polymer articles and also in the deterioration of physical properties. The secondary coating layer is believed to influence the rate at which the antimicrobial component diffuses from a dispersed particle into the polymer matrix. The small residual porosity of the silica or alumina coating, for example, also allows the antimicrobial component to diffuse through at a slow controlled rate thus extending the duration of the antimicrobial activity. Further, the ability to adjust the dispersibility of the particulate compositions of this invention both increases their use efficiency and improves the quality of the product. The antimicrobial particles may further comprise a tertiary coating layer of a hydrous metal oxide, which is much less agglomerated and disperse readily in polymers. For example, a tertiary coating of hydrous alumina or magnesia will raise the isoelectric point of the composition. The control of the isoelectric point between about 5.5 and about 9.5 is beneficial in facilitating the dispersion and/or flocculation of the particulate compositions during plant processing and in their end use applications. This both increases the use efficiency of the antimicrobial powders and improves the quality of the polymer composites. Enhanced dispersibility also can be impacted by micronizing the product with small levels, e.g., 0.1 to 1% of organic dispersion aids. Dispersion aids may be incorporated either with the antimicrobial powders or in the process for incorporating them in polymers.

A further aspect of the invention is processes for preparing the antimicrobial composition and enhancing dispersibility comprising the steps of:

(a) forming an aqueous suspension of core material particles;

(b) depositing a first coating of the desired antimicrobial component or components on the core particle surface using suitable precipitation reactions;

(c) depositing a secondary protective silica and/or alumina coating by adding an alkali metal silicate or aluminate to the suspension and maintaining the pH between specified limits;

(d) optionally applying an additional coating of a hydrous metal oxide by treatment of the suspended particles with an appropriate salt and maintaining the pH between specified limits;

(e) recovering the solids, washing free from water soluble species and drying; and (f) optionally adding a micronizing/dispersion aid to the dried particles prior to micronizing with superheated steam or air.

Another aspect of the invention relates to a polymeric article and processes for producing the same. Products incorporating the particulate composition of this invention have antimicrobial properties by virtue of the particulate antimicrobial compositions that are incorporated therein. The particulate antimicrobial compositions of this invention may be employed in a variety of products such as paints, coatings, caulks, grouts, mortar, cements and masonry products and shaped polymeric articles including, but not limited to, films, membranes, fibers, and mono-filaments including but not limited to mono-filaments for brushes. In many applications, the compositions of this invention can be used to replace all or part of fillers and/or pigments normally used in the product. For example, if $TiO_2$ is selected as the core material, then the resulting powder, when incorporated into a fiber, will deluster the fiber as well as confer antimicrobial activity. The antimicrobial particulate compositions of this invention are particularly useful when incorporated in a polymer carrier matrix composite. The physical properties of such composites are similar to those of the polymers themselves. Many different polymers can be used in the present invention.

Yet another aspect of the invention relates to a method for controlling microorganisms and various applications based on the use of the aforementioned antimicrobial materials.

DETAILED DESCRIPTION OF THE INVENTION

Antimicrobial Composition and Preparation

The invention relates to novel particulate antimicrobial powder compositions comprising inert inorganic particles having a first coating of a metal or metal compounds and a second coating layer of silica, silicates, borosilicates, aluminosilicates, alumina or mixtures thereof.

The inorganic particles, i.e., core material may be any of the oxides of titanium, aluminum, zinc, copper; the sulfates of calcium, strontium, barium; zinc sulfide; copper sulfide; zeolites; mica; talc; kaolin; mullite or silica. Lead or mercury compounds are contemplated equivalent core material but may be undesirable due to toxicity levels. Titanium dioxide and barium sulfate are the preferred core material with titanium dioxide being most preferred. Either crystalline form, anatase or rutile titanium dioxide is suitable for use in the present invention. The average diameter of the core material is between 0.01 and 100 microns, preferably in the range 0.1 to 5 microns. In general, core materials in the sub-micron size range are preferred, since the resulting antimicrobial composition can be distributed more uniformly throughout a polymer matrix.

The first coating conferring antimicrobial properties may be metallic silver or copper or compounds of silver, copper and zinc which have extremely low solubility in aqueous media. The antimicrobial component may also be an alloy of silver with copper or zinc. The antimicrobial component should release silver, copper or zinc ions at an effective level of antimicrobial activity, e.g., a minimum of 2 log reduction within 24 hours in a shake flask test, over a prolonged period, such as months or preferably years. Components which meet these criteria are silver, silver oxide, silver halides, copper, copper (I) oxide, copper (II) oxide, copper sulfide, zinc oxide, zinc sulfide, zinc silicate and mixtures thereof. Mixtures of silver with zinc silicate and silver with copper (II) oxide are preferred. The amount of antimicrobial component on the core particle is in the range of 0.05 to 20% by weight, preferably 0.1 to 5% by weight based on the particle core material. A surprising feature of the present invention is that these powders confer activity at loadings of the metals which are substantially lower than those achieved by the prior art materials. This is achieved despite the use of protective coatings to encapsulate the antimicrobial components. In carrying out this invention, the core particles may also be optionally precoated with alumina in the amount of about 1 to 4% to ensure good antimicrobial properties after precipitation of the antimicrobial components.

The secondary protective coating is selected from silica, silicates, borosilicates, aluminosilicates, alumina, aluminum phosphate, or mixtures thereof. The secondary coating functions as a barrier between the antimicrobial particle and a polymer matrix in which it may be incorporated, minimizing interaction with the polymer. This secondary coating also is believed to influence the rate at which the antimicrobial component diffuses from a dispersed particle into the polymer matrix.

The secondary protective coating layer corresponds to 0.5 to 20% by weight based on the core material, and preferably, e.g., 1 to 5% by weight of silica or, e.g., 1 to 6% by weight of alumina in the coated particle composition. It will be appreciated by those skilled in the art that if fine particles of a core material are employed in carrying out the invention, the practitioner should assure total surface coverage of the first coated core material. The protective layer of silica or alumina can be quite dense although it must be sufficiently porous to permit diffusion of the antimicrobial metal ions through the coating at a slow rate, while functioning as a barrier which limits interaction between the antimicrobial component and the polymeric matrix in which it is distributed. Silica is a preferred coating material because of the relative ease with which dense, uniform coatings can be obtained. Silica-coated particles may have a low isoelectric point and may tend to be difficult to disperse in organic materials. The isoelectric point represents the pH at which a particle surface carries zero electric charge. Control of the isoelectric point between 5.5 and 9.5 is beneficial in facilitating the dispersion and/or flocculation of the particulate compositions during plant processing and in their end use applications. Therefore, for particles coated with silica or related materials with a low isoelectric point, a tertiary coating of hydrous alumina or magnesia, or other metal oxide may be added to raise the isoelectric point. For example, hydrous oxides of Al, Mg, Zr and the rare earths, may bring the isoelectric point into the range of 5.5 to 9.5. Hydrous alumina, typically as a mixture of boehmite (AlOOH) and amorphous alumina ($Al_2O_3H_2O$), is a preferred tertiary coating material. Isoelectric points in a preferred range of 5.5 to 8.8 can readily be obtained with alumina coatings. For higher isoelectric points, magnesia is preferred. Dispersion aids may be incorporated either with the antimicrobial powder composition or in the process for incorporating them in polymers to facilitate dispersion in end use applications.

In an alternative embodiment of the invention, alumina may be selected as the secondary protective coating and a tertiary coating may not be needed to adjust the isoelectric point. When alumina is used as the protective coating, the isoelectric point of the resulting powder typically will be in the preferred range.

The process for preparing the antimicrobial compositions of the invention comprises the steps of first forming a stirred aqueous suspension of the core material in which the concentration of solids is between 10 to about 50 weight percent. The core material employed in the process consists of fine particles of an inorganic composition selected from a group comprising the oxides of Ti, Al, Zn and Cu, the sulfates of Ca, Sr and Ba, zeolite, mica, talc, kaolin or silica. These compositions are essentially insoluble in water or aqueous environments. Titanium dioxide and barium sulfate are the preferred core materials for use in the process of the invention with titanium dioxide being most preferred. Either crystalline form, anatase or rutile may be used. The average particle size of the core material can extend over a wide range from 0.01 to 100 microns depending on the shape of the particle, although in most cases the range is 0.1 to 5 microns. The particles can have a wide variety of shapes, e.g. equiaxial, acicular or platelet. Smaller size equiaxial shaped particles are preferred since they give a more uniform distribution of antimicrobial effectiveness when they are incorporated in a polymer matrix. Generally, the finely divided core material particles will exhibit a specific surface area in the range of from 0.1 to 100 $m^2/g$. Best results are achieved when the core material particles have a specific surface area of from 1 to 20 $m^2/g$.

Next, the antimicrobial components are formed by precipitation reactions conducted in the stirred aqueous suspension of core material so that the core particles become coated with the precipitated antimicrobial composition. The antimicrobial component is selected from a group comprising Ag, $Ag_2O$, AgCl, AgBr, AgI, Cu, CuO, $Cu_2O$; CuS; ZnO; ZnS; $ZnSiO_3$ and their combinations such as Ag/CuO, Ag/$ZnSiO_3$ and alloys of silver with copper or zinc. The concentrations and amounts of reactants used in applying the antimicrobial components to the core particles are such that the former amounts to between 0.05 and 20% by weight, preferably 0.1 to 5% by weight of the supporting core particle. The antimicrobial metal constituent is added to the suspension as a water soluble salt such as a nitrate or acetate together with an appropriate water soluble reagent to precipitate the desired antimicrobial compound. For example, $Ag_2O$ is an effective antimicrobial agent and it can be precipitated by adding $AgNO_3$ to a stirred aqueous suspension of core particles while maintaining the pH in the range of 5 to 9.

Reagents used for this purpose are hydroxides of ammonia, alkali metals or alkali metal silicates. When metallic silver or copper are to be deposited on the core material, water soluble reducing agents such as formaldehyde, hydrazine or sodium nitrate are used to reduce the cation to the metal. When the antimicrobial component comprises more than one species, such as Ag and $ZnSiO_3$, individual species may be precipitated successively or concurrently depending upon the compatibility of the reagents used to precipitate the different species. The choice of reagents, order of precipitation and procedural conditions can be employed by one skilled in the art.

The next step in the process is the application of a secondary protective coating, for example, silica or alumina to the antimicrobial particles in the aqueous suspension.

In the case of a silica coating, active silica is added to the agitated aqueous suspension heated to a temperature between 60° and 90° C. while maintaining the pH of the suspension in the range of 6 to 11. The procedure is described in detail in U.S. Pat. No. 2,885,366 which issued on May 5, 1959 to Iler, the teachings of which are incorporated herein by reference. Active silica, a low molecular weight form of silica, such as silicic acid or polysilicic acid, may be added to the suspension, or formed in situ as by the continuous reaction of an acid with an alkali silicate. Potassium silicate is generally preferred since the potassium ion has little tendency to coagulate active silica. The bulk commodity is also more stable, which is advantageous from the standpoint of shipping and storing. The silica content of the coated composition is between 0.5 and 20% by weight and most commonly it is between 1 and 5% by weight.

During the silica deposition it is desirable to maintain substantially uniform conditions in the reaction zone to minimize precipitation of free silica gel. This is best accomplished by maintaining good agitation and introducing the reactants in a manner which does not allow local overconcentration. The pH is allowed to fall gradually to about 6 as the process is completed and the slurry is then cured to permit completion of the deposition of silica onto the surface of the antimicrobial particles. The curing step consists of holding the slurry at temperatures between 60° and 90° C., preferably between 75° and 90° C., for from about one-half to two hours, preferably about one hour, while maintaining the pH of the agitated slurry between 6 and 7.5.

Alternatively, the antimicrobial particles may be coated with alumina. This is accomplished by the addition, to the agitated aqueous suspension of the antimicrobial particles heated to between 60° and 90° C., of an alkali aluminate solution or other soluble aluminum salt, e.g., aluminate nitrate while maintaining the pH in the range 6 to 11 by the concurrent addition of acid or base, as required. Sodium aluminate is preferred, because it is commercially available as a solution, such as Vining's Solution. It is desirable to increase the density of the amorphous alumina phase in the coating by the addition of polyvalent anions selected from the group consisting of sulfate, phosphate and citrate. As in the case of the silica coating a small residual porosity is necessary to allow the antimicrobial species to diffuse through the protective coating. The alumina content of the coated composition is between 0.5 and 20% by weight and preferably between 1 and 6% by weight. The concentration of polyvalent anion in the suspension is about 0.5% by weight based on the alumina used to coat the particles.

The product is then recovered as a dry powder, consisting of particles coated with silica, alumina or silica/alumina, by filtration or centrifugation combined with aqueous washing to remove soluble salts. A vacuum rotary-type filter is particularly suitable since washing can be carried out without removing the product from the filter.

Washing is continued until the filtrate is quite free from soluble ions. The washed cake is then dried in an air or vacuum oven. A preferred commercial method of drying the product is spray drying. The product may be passed through a micronizer with either heated air or superheated steam, preferably at temperatures below 350° C.

It would be appreciated by those skilled in the art that the micronizing/dispersion aid could also be added prior to drying of the recovered and washed solids.

In carrying out the invention and enhancing dispersibility, control of the isoelectric point between 5.5 and 9.5 is beneficial. The isoelectric point of the particles can be adjusted within the range 5.5 to 8.8 by using alumina as the secondary or tertiary coating. However, it may be preferred for other reasons to use silica or other low isoelectric point material for the protective coating. In which case, a tertiary coating is desired to adjust the isoelectric point to the range of 5.5 to 9.5. The higher isoelectric point improves the dispersibility of the antimicrobial composition in all systems, e.g., water systems.

The isoelectric point represents the pH at which the surface of the particles carries zero electric charge. The isoelectric point is determined by measuring the electrophoretic mobility of the particles in a dilute suspension. An automated electrokinetics analyzer, such as the Pen Ken System 3000, manufactured by Pen Ken, Inc., Bedford Mills, N.Y. is used for this purpose. Measurements are made at different pH levels and by graphically plotting the results, the isoelectric point, i.e., the pH at which the Zeta potential is zero, can be determined.

An optional hydrous metal oxide tertiary outer layer is applied as a final coating process. A solution of a salt which contains the desired metal is added to the agitated aqueous suspension at a temperature between 60° and 90° C., while controlling the pH of the suspension with either acid or base within the range of 6 to 11, preferably 7.0–9.0. Metals contemplated for use according to the invention are those whose hydrous oxides have high isoelectric points, i.e. in the range of 5.5 to 9.5.

The hydrous metal oxide is selected from the group consisting of alumina, magnesia, zirconia and rare earth metal oxides, with alumina, particularly boehmite AlOOH and amorphous alumina $Al_2O_3$ $H_2O$, and magnesia which are most preferred for reasons of ease 5 of application, availability and economy. Sodium aluminate is a preferred source of aluminum, and magnesium chloride is a preferred source of magnesium. The use of alumina allows adjustments of the isoelectric point up to about 8.8 while the use of a magnesium precipitate allows adjustments to up to about 9.5. When sodium aluminate is used, the pH of the suspension is preferably maintained in the range of 8 to 8.5. When magnesium chloride is used, the pH is preferably maintained at about 9. Other water 5 soluble salts may be used according to the invention such as chlorides, nitrates, and acetates. Where an acid salt is used as a source of metal, a strong alkali, such as sodium hydroxide or potassium hydroxide, can be added to the aqueous suspension to maintain the pH within the desired range. If a basic salt is used as the source of metal, a strong acid, such as hydrochloric acid, can be added to the aqueous suspension to maintain the pH within the desired range. Coating can be accomplished at room temperature, but the best results are obtained when the temperature of the suspension is maintained in the range of from 60° to 90° C.

The product is recovered as a dry powder, comprising the core material having the antimicrobial agent and the hydrous metal oxide/silica or alumina coating using the procedures previously described. It has also been found to be advantageous, both from the standpoint of improving the rate of compounding antimicrobial compositions of the invention in polymer systems and of forming more uniform dispersions, to add dispersion aids to the powders. The benefit derived from the dispersion aid is greater in those powders wherein the particles have not been given a hydrous metal oxide coating. Dispersion aids which can be used effectively in this aspect of the invention are organic esters, polyols and polyester oligomers. Dioctyl azelate is a preferred dispersion aid for the antimicrobial compositions of the invention. The amount of dispersion aid added to the antimicrobial powder is between 0.2 and 3% by weight with 0.5 to 1% being sufficient in most cases. The dispersion aid is normally intimately mixed with the antimicrobial powder, in standard equipment such a "v" or ribbon blender, prior to the micronizing step.

Antimicrobial Polymer Articles of the Invention and Processes for Producing the Same A further aspect of this invention relates to polymer articles having antibacterial properties by virtue of particulate antimicrobial compositions being incorporated into the polymer matrix. The particulate antimicrobial compositions of this invention may be employed in a variety of products such as paints, coatings, caulks, grouts, mortar, cement and masonary products and shaped polymeric articles including, but not limited to, films, membranes, fibers and monofilament, including but not limited to mono-filaments for brushes. The antimicrobial powders that are made by the above processes can be incorporated as fillers or surface treatments for plastics, fibers, rubbers and other high molecular weight natural and synthetic materials. They are very effective as broad-spectrum antibacterials, antifungals and disinfectants and they have excellent durability, due to their low solubility in water.

The organic polymers from which the articles are fabricated include synthetic, natural and semi-synthetic organic polymers. Examples of polymers that can be used to practice this invention include, but are not limited to, aliphatic and aromatic polyesters, including polyethylene terephthalate, polybutylene terephthalate, polyethylene isophthalate, polyhexamethylene terephthalate, polylactic acid, polyglycolic acid, and liquid crystalline polymers for high performance resins and fibers; polyester block copolymers; aliphatic and aromatic polyamides including nylon 6, nylon 66, nylon 610, nylon 11, nylon 12, nylon 1212, poly-p-phenylene terephthalamide, poly-m-phenylene isophthalamide; copolymerised polyamides; polyolefins including polyethylene, polypropylene, and copolymers thereof; vinyl polymers, including polystyrene, polyacrylonitrile, polyvinylalcohol, polyvinyl acetate, polyvinylchloride, polyvinylidene chloride, ABS resins and acrylic resins; copolymers of ethylene and vinyl acetate; fluorocarbon polymers, including polytetrafluoroethylene, polyvinylidene fluoride and polyvinyl fluoride; polyurethanes; segmented polyurethane elastomers, spandex or elastane elastomers; polyethers, including polyacetals; polyketones, polyetherether ketone (PEEK), polyether ketoneketone (PEKK); polyether and polyester block polymers; polysulfides; polysulfones; polysiloxanes such as polydimethyl siloxane; polycarbonates; thermosetting synthetic polymers such as phenol-formaldehyde copolymer, polyurethane, polyesterurethane, polyetherurethane, polyetherurethaneurea, polyesterurethaneurea; natural polymers such as cellulosics, cotton and wool; and regenerated or semi-synthetic polymers such as rayon, cuprammonium rayon, acetate rayon, triacetate rayon, reconstituted silk and polysaccharides. This group includes reasonable copolymers, terpolymers and blends of many of the species listed. Spandex is defined herein to refer to a fiber or filament made from a long chain synthetic polymer that comprises at least 85% by weight of a segmented polyurethane.

The polymer articles of this invention can be, for example, in the shape of films, fibers, powders, granules or articles made therefrom such as containers, pipes and monofilaments for brushes. When a high degree of antimicrobial effect is desired, the moulded article preferably has a large surface area.

A polymer article of the invention having antimicrobial properties is comprised of at least one of the aforementioned particulate antimicrobial compositions and at least one organic polymer. The antimicrobial composition accounts for 0.1 to 60% by weight, preferably 0.1 to 15% by weight of the polymer article, and most preferably 0.3 to 2% weight of the polymer article.

If the antimicrobial composition is incorporated in an amount less than about 0.1% by weight, the polymer article has insufficient antimicrobial activity for any useful applications. However, it will be appreciated by those skilled in the art that if extremely fine particles are incorporated into the polymer matrix, then less than about 0.1% may be acceptable. Above about 60% by weight there is no significant increase in the antimicrobial activity of the polymer article and the physical properties of the polymer article start to show some deterioration. This limits the usefulness of the article. Furthermore, the incorporation of high levels of the antimicrobial composition is undesirable from an economic standpoint and because of undesirable effects on the properties of the composite. A preferred upper level for the antimicrobial component is about 15% weight below which level there is an optimum combination of antimicrobial activity, polymer article properties and cost-efficiency.

When a polymer article according to the present invention has a relatively large thickness, such as containers, pipes, granules or coarse fibers, the particle size of the antimicrobial powder may be in the range of a few microns to tens of microns or even up to a hundred microns. When fibers or films are molded as an article according to the present invention, preference is given to a smaller size particle, for instance, a particle size of 5 microns down to a one hundredth of a micron (ten nanometers), especially less than 2 microns, is commonly employed for fibers intended for use in clothing.

The polymer articles according to the present invention may contain other additives as well as antimicrobial compositions. They may contain, for example, polymerization catalysts, stabilizers, delustering agents, optical whitening agents, organic or inorganic pigments, inorganic fillers, plasticisers and so on. It is also possible that the antimicrobial particles themselves can fulfill a dual role and provide the benefits of some of the aforementioned additives.

In many applications, the compositions of this invention can be used to replace all or part of fillers and/or pigments normally used in the product. This invention also relates to bifunctional powders, which can be used to deluster polymeric fibers as well as to provide antimicrobial properties. For example, if TiO$_2$ is selected as the core particle, then the resulting powder, when incorporated into a fiber, will deluster the fiber as well as confer antimicrobial activity. The antimicrobial particulate compositions of this invention are particularly useful when incorporated in polymer matrix. The physical properties of such composites are similar to those of the polymers themselves. Many different polymer compositions can be used in the present invention.

Conventional procedures for incorporating powders in polymer compositions may be used to prepare the polymer articles of the invention. The antimicrobial powders may be added to a monomer or to an intermediate product prior to polymerization. However, generally they are mixed or compounded with a finished polymer before it is shaped into a useful article. Precoating of antimicrobial particles with polymer greatly facilitates incorporation of the particles in the bulk polymer. This may be done, for example, by slurrying the antimicrobial powder with a solution of the polymer, then removing the solvent by drying. About 1 to 5% by weight of polymer based on the coated powder is suitable for this purpose.

The polymer articles are fabricated from the antimicrobial polymer compositions and mixtures of them using well known procedures. These include, but are not limited to, for example, coating, molding, extruding, spinning and melt blowing. If it is desirable to have the antimicrobial component predominantly at the surface of the article this can be accomplished by heating the finished article to a temperature at which the surface becomes sticky or tacky and immersing it, or drawing it through a free flowing bed of antimicrobial particles or sprinkling said particles onto the heated surface. Alternatively, a tacky surface can be produced by dipping the article in an appropriate solvent. On cooling the article the surface sets with the antimicrobial particles embedded in it. Dispersion aids may also be incorporated in the process of forming the polymer carrier matrices or articles.

Process for Controlling Microorganisms

The present invention also provides processes for controlling microorganisms using the antimicrobial materials of the invention. Microorganisms can be controlled in a variety of media by contacting an effective amount of the antimicrobial material with a microorganism. A convenient medium is an aqueous medium although a gaseous medium would behave similarly. Contacting the skin or other parts of a mammal with an effective amount of the antimicrobial material would also be expected to control microorganisms.

The antimicrobial material of the present invention controls a broad spectrum of microorganisms. The material has been found to be useful in controlling bacteria, myceteae and viruses in the Shake Flask Test described, infra. The antimicrobial material would also be expected to control algae, protozoa, viroids and prions in a similar manner.

By the term "bacteria" is meant eubacteria and archaebacteria. Eubacteria include fermicutes, gracilicutes and ternicutes. Gracilicutes include gram-negative, facultatively anaerobic rods. Gram-negative, facultatively anaerobic rods include Enterobacteriaceae. Enterobacteriaceae include Klebsiella and Escherichia. Klebsiella include *Klebsiella pneumoniae* and Escherichia include *Escherichia coli*. Fermicutes include the group gram-positive cocci, and the group endospore-forming rods and cocci. Gram-positive cocci include Micrococcaceae. Micrococcaceae include Staphylococcus and Staphylococcus includes *Staphylococcus aureus*. Endospore-forming rods and cocci include Bacillaceae. Bacillaceae includes which includes *Bacillus circulans*. All references herein to bacteria are in accordance with Bergey's Manual of Systematic Bacteriology, Williams & Wilkens, 1st ed. Vol. 1–4, (1984).

The term "Myceteae" includes Amastigomycota. Amastigomycota include Deuteromycotina which includes Deuteromycetes. Deuteromycetes include Aspergillis and Candida. Aspergillis includes *Aspergillis niger* and Candida includes *Candida albicans*.

The term "virus" includes bacteriophage. Bacteriophage includes T-series bacteriophage which includes T-even bacteriophage such as bacteriophage T4.

Applications

Examples of suitable applications comprising the antimicrobial articles and materials of the present invention include medical applications, such as, melt blown antimicrobial fibers for sterile filters dental devices, food wrap, floor coverings, such as carpet backings, textile applications such as sportswear, intimate apparel, shoe linings, socks, undergarments and the like and coatings. More specifically, examples of medical devices include wound closure devices, such as those sutures which are generally described in "Gore-Tex" Suture Bulletins, W. L. Gore & Assoc., Inc. (1986). Examples of devices for purifying or sterilizing aqueous solutions include those which are generally described in Gelman Sciences Process Microfiltration Catalog, (April 1986). Similarly, examples of devices for purifying or sterilizing a gas include those which are generally described in "Nonwovens in Filtration (1987) Worldwide," Filter Media Consulting, Inc., (April 1988). Examples of catheters include those generally described in "MEDSPEC 1989," Medical Device Register, Inc., (1989). Examples of suitable devices for storing, transporting or dispensing sterile solutions, devices for controlling odors, wound dressings and garments such as gowns and masks are generally described in "Hospital Supply Index," Product Analysis, Vol 1A and 1D, IMS America Ltd., (Third Quarter 1986). Examples of medical implants are generally described in "The Orthopedic Implants and Allied Products Markets Outside the U.S.," Frost & Sullivan, Inc., (April 1985). Examples of floor coverings, such as carpet backing, are generally described in Edwards, U.S. Pat. No. 3,563,838, Hendersen, U.S. Pat. No. 3,821,062 and Peterson, U.S. Pat. No. 3,502,538. Examples of food wraps are generally described in Chemical Week, Mar. 13, 1983, p. 11. Examples of coatings are generally described in Biomedical Business International, Mar. 2, 1988, pp. 37–38 (Medical), Textil Praxis International, foreign edition with English supplement, 1980, vol. 35, pp. XVI–XXIII (Consumer), and West Marine Products Catalog, (P.O. Box 1020 Watsonville, Calif. 95077) (Summer 1989) pp. 99–100 (Marine). Examples of tests in which a preservative comprising the antimicrobial material of the present invention could be used are described in "United States Pharmacopeia, Microbiolgial Tests (51)." Antimicrobial Preservative Effectiveness, Vol. XXII pp. 1478–1479 (1990).

Preparation of Polymer Samples for Testing

For polymers which are stable in a melt and whose melt viscosity is not too high (e.g., nylon 6,6) melt spinning is the preferred method. In continuous operation, injection of the antimicrobial particulate just prior to spinning would be typical. A particularly convenient laboratory variant of melt spinning called press melt spinning allows one to produce very small samples of fiber for evaluation. In this process the polymer is ground to a powder (typically until it will pass through a 100 mesh screen) and mixed with the dry powder additive at the desired concentration (1% by weight for example). The mixture is dried at >70° C. under vacuum overnight and is then compression molded into a cylindrical plug at the appropriate molding temperature for the type of polymer being used. The plug is removed from the mold and placed in a fiber spinning unit. Under hydraulically applied ram pressure, the polymer plug is melted and extruded through a spinneret into filaments which can then be drawn and wound up on collection bobbins for antimicrobial testing.

If the polymer is soluble in a solvent then wet or dry spinning become alternative processes for consideration. In either process, the antimicrobial particulate is dispersed (at the desired concentration) in the polymer solution prior to spinning. The solution is extruded through a spinneret and recovered as fiber either by evaporation of the solvent (dry spinning) or coagulation of the polymer by a non-solvent (wet spinning). Further processing as practiced in the art such as extraction, drawing, drying, or crystallizing may be required.

Other fiber forming processes, including, but not limited to, flash spinning, dispersion spinning, air gap spinning, and centrifugal spinning may be useful in appropriate polymer systems.

The polymeric articles evaluated in the examples of this invention were prepared as follows:

Nylon 66—dead bright nylon 66 powder (46 HRV) was admixed with the indicated additives and melt spun into fibers.

Polyethylene—high density polyethylene (0.85 MI) was admixed with the indicated additives and flash spun from solution in difluorochloromethane to produce a plexifilamentary web for testing.

Poly-m-phenylene-isophthalamide—the indicated additives were admixed to a solution of poly-m-phenylene isophthalamide (I.V.=1.5) in dimethylacetamide/$CaCl_2$. This solution was then dry spun and the resultant fibers washed and drawn 4× before testing physical properties.

Polyethylene terephthalate—dead bright polyethylene terephthalate powder (21.4 HRV) was admixed with the indicated additives and melt spun into fibers.

Segmented polyurethane urea copolymer—the indicated additives were admixed to dimethylacetamide solutions of segmented polyurethane-urea copolymer containing a polyester soft segment or other soft segments. These solutions were either cast into films by solvent evaporation or wet spun into an aqueous coagulation bath to produce fibers for evaluation of antimicrobial activity.

Evaluation of the antimicrobial properties in the Examples was performed using the following test methods.
(1) Leaching Test Method for Antimicrobial Powders Polyethylene bottles (60 ml) or sterile polystyrene centrifuge tubes (50 ml) are cleaned by rinsing with a 50/50(V/V) nitric acid/deionized water solution. Following the nitric acid rinse, the bottles are rinsed several times with deionized water to ensure complete removal of the acid. Into these cleaned bottles are added 50 ml of either deionized water or physiological saline (0.8%). 0.2 gm of neat test sample is then added, shaken briefly by hand and the 0.4% dispersion allowed to sit at ambient temperature for 24 hours. After the specified period, the dispersion is filtered through a sterile 0.22 micron filter containing a cellulose acetate or cellulose nitrate membrane and sterile storage bottle and cap. The aqueous leachate is then analyzed for trace metals via either Inductively Coupled Plasma-Atomic Emission Spectroscopy (ICP-AES) or Flame Atomic Absorption (AA). Elemental analysis is reported in ppb.

(2) Scour and Dye Procedure

Samples were secured in cheese cloth and prescoured and dyed in an Abiba laboratory atmospheric dyer(Ahiba, Inc. Type WBRG7) using standard nylon levelling acid dye procedures as described in Du Pont Technical Bulletin NY-12(except as noted below). Prescouring was done at 71° C. for 15 minutes using 0.25 g/l each of Merpol DA and TSPP. Dyeing was done near the boil (99° C.) for 1 hour and at pH 6 using leveling acid dyes and no UV inhibitors. Samples were then whiz dried. Aliquots of scour and dye baths were retained for heavy metal analysis.

(3) Washing Procedure

Samples were secured in cheese cloth and washed in a Kenmore washer (Model 82110084) as specified in AATCC test method 150–1987 with the exception of using a different type and less amount of detergent, i.e., used 30±5 g of Tide instead of 90 ±0.1 g of AATCC standard detergent 124. Samples were tumble dried at 68–°71° C. in a Kenmore dryer (Model 95018502). All samples were washed 20 times with drying after each wash.

(4) Shake Flask Test for Antimicrobial Activity

Antimicrobial activity was measured using the Shake Flask Test described generally in U.S. Pat. No. 4,708,870 and outlined in Malek and Speier, The Journal of Coated Fabrics, Vol. 12, July 1982, pp. 38–45.

The Shake Flask Test requires the test material to be in a form having a high surface area to weight ratio. Articles having the form of powders, fibers, and thin films have proven to be acceptable.

The bacterial inoculum for the Shake Flask Test was prepared by transferring 2.0 ml of an overnight broth culture to a 300 ml nephyloculture flask (Bellco Glass Inc., Vineland, N.J.) containing 100 ml of Tryptic Soy Broth (TSB) (Remel, Lexena, Kans.). This flask was incubated at 37° C. with shaking (ca. 200 rpm). Growth of the culture was determined during incubation using a Klett-Summerson photoelectric colorimeter (Klett MFg. Co., NY, N.Y.). When the culture reached late-log phase (185–200 Klett units for *Klebsiella pneumoniae* ATCC 4352), appropriate dilutions were made with sterile 0.2 mM phosphate buffer (pH 7).

This inoculum was then placed into sterile, disposable 250 ml Erlenmeyer flasks (Corning Glass Co., Corning, N.Y.) containing 0.75 g of the material produced by the process of this invention or a suitable control material as indicated below. Each flask contained a known concentration of bacteria in a final volume of 75 ml phosphate buffer.

The initial concentration of bacteria used in the various examples was determined by serial dilution of the inoculum (0.2 mM Phosphate buffer, pH 7) and plating in triplicate on Trypticase Soy Agar (TSA) plates (sold commercially by BBL, Cockeysville, Md.). The flasks were shaken on a Burrell wrist action shaker (Burrell Corp., Pittsburgh, Pa.). A 1.2 ml aliquot was removed from each flask after shaking for 1 hour (or other appropriate time interval as indicated). Duplicate petri plates containing TSA were inoculated via spread plating with 0.1 ml each of the sample. The remaining 1.0 ml was serial diluted and plated in duplicate. The TSA plates were incubated at 37° C. for 18 to 24 hours. Plates having between 30 and 300 colonies were counted and the bacterial concentration determined from the mean of the plate counts. If none of the plates contained at least 30 colonies, all colonies were counted and the bacterial concentration determined from the mean of the plate counts. Below the limit of detection of the procedure described herein, the colony count was said to be zero.

Antimicrobial activity was determined by the formulas:

kt=log10(Co)-log10(Ct+1)

Dt=log10(CFt)-log10(Ct+1)

where:

Co=initial concentration of bacteria (cfu/ml) in test flask at time zero

Ct=concentration of bacteria (cfu/ml) in test flask at time t (one is added to the number to avoid calculating the log of zero), CFt=concentration of bacteria (cfu/ml) in control flask at time t, and cfu/ml=colony forming units per milliliter.

The relationship between percent reduction and log reduction is conveniently seen by reference to the following:

| % Reduction | Kt | Log Reduction |
| --- | --- | --- |
| 90 | 1 | 1 |
| 99 | 2 | 2 |
| 99.9 | 3 | 3 |
| 99.99 | 4 | 4 |
| 99.999 | 5 | 5 |

In all the Examples, the organic polymer was tested substantially free of fiber finish.

(5) Minimum Inhibitory Concentration (MIC) Procedure

Cultures and inocula preparation for bacteria and yeast were performed as described previously except cells were harvested by centrifugation, washed, and resuspended in saline. Aspergillus suspensions were prepared by harvesting mycelia from 12 day TSA plate cultures incubated at room temperature. Plates were flooded with 0.2 mM phosphate buffer (pH 7) containing 0.05% Tween® 80 and scraped with a sterile glass rod. This suspension was transferred to a sterile Jar containing glass beads and shaken to release spores from the mycelial clumps. The contents were filtered through sterile glass wool to remove hyphal fragments. Spores were then harvested by centrifugation (19000× g), washed, and resuspended in saline. The concentration of spores was determined by plating the suspension prior to use.

Cultures were diluted and appropriate aliquots added to each saline dilution tube in the series to produce a final concentration of approximately 1.0E+05 cfu/ml. Appropriate quantities of test sample were weighed and added to the initial test tube in the series. This was vortexed several times to ensure a homogeneous mixture and serial dilutions (10 fold) performed. The test tubes were shaken at 200 rpm at 37° C. for 24 hours. After 24 hours, a sample was removed from each tube via an inoculationg loop (1 ul volume) and streaked onto the surface of a TSA plate. Plates were incubated for 24 hours at 37° C. Antimicrobial activity was evaluated by visually determining the number of colonies in the initial streak across the agar plate. A "+" rating was assigned to plates having growth. A "–" rating represents plates without any colonies. The MIC was based upon the minimum concentration of test compound which resulted in no microbial growth on the plate.

The present invention is further described in the following examples and comparative showings which illustrate the advantages of the invention. They should not be construed as limiting in any way the scope of the invention.

EXAMPLES 1–11

Preparation of Particulate Antimicrobial Compositions

Example 1

This example describes the preparation of a titanium dioxide ($TiO_2$) pigment powder coated successively with silver (Ag), zinc silicate ($ZnSiO_3$), silicon dioxide ($SiO_2$) and hydrous alumina. The product was a white powder readily dispersable in organic polymer systems and providing them with antimicrobial properties.

The equipment consisted of a five gallon polyethylene container equipped with a paddle stirrer, burettes to introduce solutions of reactants and a pH probe. The container was mounted on a heating plate.

First Stage:

While stirring 12 liters of deionized water at 75° C., 5000 g of pigment grade $TiO_2$ (Du Pont R-101) was added to form a slurry containing about 415 g/l. A solution of 18.75 g $AgNO_3$ in 50 ml $H_2O$, (J. T. Baker, Reagent Grade $AgNO_3$), was added at a uniform rate to the slurry stirred at 75° C. over a period of 10 minutes. After stirring for an additional 5 minutes, the pH was adjusted to 9.0 by the addition of $NH_4OH$. 10 ml of hydrazine, (Aldrich 35 weight percent in water), was diluted with 50 ml water and the solution was added to the slurry at a uniform rate over a 30 minute period, to convert the silver oxide to metallic silver. The slurry was stirred at 75° C. and a pH of about 8.5 for a further 30 minutes.

Second Stage:

Solutions were then prepared, consisting of 20 g $ZnCl_2$ (J. T. Baker, Reagent Grade), in 100 ml water and 625 g $K_2SiO_3$ (Philadelphia Quartz, #6 KaSil; 25 weight percent $SiO_2$), diluted to 1000 ml with water. 93.75 ml of the $ZnCl_2$ solution and 250 ml of $K_2SiO_3$ solution were added concurrently at a uniform rate to the stirred slurry over a 30 minute period, maintaining the temperature at 90° C. and the pH at 9.5. The remaining 750 ml of $K_2SiO_3$ solution was added at a uniform rate over a 30 minute period followed by maintaining the temperature at 90° C. and the pH at 9.5 for a further 30 minutes with continuous stirring to cure the silica coating.

Third Stage:

The slurry was then cooled to 75° C. and the pH adjusted to 8.2 with HCl. Next, 300 ml of Vinings solution $NaAl(OH)_4$, (Stanbach-Vinings Corp. 0.385 g $Al_2O_3$/ml), was added at a uniform rate over a period of one hour maintaining the temperature at 75° C. and the pH at 8.2. The slurry was stirred at 75° C. and a pH of 8.2 for a further 30 minutes cure period.

The solids were recovered by filtration using a vacuum filter, and washed with deionized water until the washings tested chloride free. The washed solids were dried in an air oven at 120° C. overnight to recover 5248 g of a free flowing white powder. The resulting powder was found by chemical anaylsis to contain 0.22 weight percent Ag, 0.37 weight percent $ZnSiO_3$, 2.75 weight percent $SiO_2$ and 2.2 weight percent $Al_2O_3$. The remainder was $TiO_2$.

Example 1B 5000 grams of the dry powder from Example 1A was blended with 1 weight percent dioctyl azelate and micronized using super heated steam at a steam to powder blend weight ratio of 3:1.

Examples 2 to 10

Using the procedure described in Example 1 a number of antimicrobial powders were prepared. Preparations 2 through 5 were conducted in a 2-liter beaker (1200 ml $H_2O$) and 6 through 10 were conducted in a 4-liter beaker (2500 ml $H_2O$). The core particles, reagents and quantities used in the first, second and third stages of the process are given in Table 1. The pH and temperature in degrees centigrade and the nominal analyses of the products are also shown in Table 1.

TABLE 1

Preparation of Antimicrobial Powders

| Example No. | 2 | 3 | 4 | 5 |
|---|---|---|---|---|
| Water ml | 1200 | 1200 | 1000 | 1000 |
| Core Particle | | | | |
| $TiO_2$ (R101) | 200 | 200 | — | — |
| ZnO (J. T. Baker Reagent Grade) (g) | — | — | 200 | 200 |
| $BaSO_4$ (Blanc Fixe) (g) | — | — | — | — |
| First Stage | | | | |
| $AgNO_3$ g/$H_2O$ ml | 3/50 | 3/50 | 5/0 | 5/0 |
| NaCl g/$H_2O$ ml | — | — | 10/50 | 10/50 |
| $N_2H_4$ (ml)/$H_2O$ (ml) | 5/0 | 5/0 | — | — |
| pH/°C. | 9.0/75 | 8.5/75 | 9.5/80 | 9.5/80 |
| Second Stage | | | | |
| $Cu(NO_3)_2 \cdot 2H_2O$ (20 g/100 ml $H_2O$) (ml) | — | 15 | — | — |
| $ZnCl_2$ (20 g/100 ml $H_2O$) (ml) | 15 | — | 15* | 15* |
| $K_2SiO_3$ g/$H_2O$ ml | 25/50 | — | 45/100 | 45/100 |
| pH/°C. | 7.0/75 | 7.0/75 | 9.5/80 | 9.5/80 |
| Third Stage | | | | |
| $NaAl(OH)_4$ (ml) | 12 | 12 | — | 12 |
| pH/°C. | 8.2/75 | 8.2/75 | — | 8.2/70 |

TABLE 1-continued

Preparation of Antimicrobial Powders

| Composition (Nominal %) | | | | | |
|---|---|---|---|---|---|
| Ag | 0.90 | 0.90 | — | — | |
| AgCl | — | — | 2 | 2 | |
| $Al_2O_3$ | 2.2 | 2.2 | — | 2.2 | |
| CuO | — | 0.45 | — | — | |
| $SiO_2$ | 2.5 | — | 4.5 | 4.5 | |
| $ZnSiO_3$ | 1.5 | — | 1.5 | 1.5 | |

| Example No. | 6 | 7 | 8 | 9 | 10 |
|---|---|---|---|---|---|
| Water ml | 2500 | 2500 | 2500 | 2500 | 2500 |
| Core Particle | | | | | |
| $TiO_2$ (R101) | 800 | — | 1000 | 800 | 750 (SCM-RG anatase) |
| ZnO (J. T. Baker Reagent Grade (g) | — | — | — | — | |
| $BaSO_4$ (Blanc Fixe) (g) | — | 800 | — | — | — |
| First Stage | | | | | |
| $AgNO_3$ (g)/$H_2O$ (ml) | 3/50 | 3/50 | 3.75/50 | 3/50 | 14.06/50 |
| NaCl (g)/$H_2O$ (ml) | — | — | — | — | — |
| $N_2H_4$ (ml)/$H_2O$ (ml) | 5/25 | 2/25 | 5/25 | 5/25 | 7.5/50 |
| pH/°C. | 8.5/75 | 8.5/75 | 9.0/75 | 8.5/75 | 9.0/75 |
| Second Stage | | | | | |
| $Cu(NO_3)_2 \cdot 2H_2O$ (20 g/100 ml $H_2O$) (ml) | 30 | 30 | 37.5 | — | — |
| $ZnCl_2$ (20 g/100 ml $H_2O$) (ml) | — | — | — | 60 | 70.31 g/200 |
| $K_2SiO_3$ g/$H_2O$ (ml) | 64/200 | 64/200 | — | 100/200 | 123.76/200 +69.0/200 |
| pH/°C. | 9.5/90 | 9.5/90 | 7.0/75 | 9.5/90 | 9.5/90 |
| Third Stage | | | | | |
| $NaAl(OH)_4$ (ml) | 48 | 48 | 60 | 48 | 45 |
| pH/°C. | 8.2/70 | 8.2/75 | 8.2/75 | 8.2/75 | 8.2/75 |
| Composition (Nominal %) | | | | | |
| Ag | 0.22 | 0.22 | 0.22 | 0.22 | 1.1 |
| AgCl | — | — | — | — | — |
| $Al_2O_3$ | 2.2 | 2.2 | 2.2 | 2.2 | 2.0 |
| CuO | 0.27 | 0.27 | 0.27 | — | — |
| $SiO_2$ | 2.0 | 2.0 | — | 2.5 | 2.1 |
| $ZnSiO_3$ | — | — | — | 1.5 | 0.85 |

*Diluted to 100 ml with 20% HCl

Example 11A

This example describes the preparation of a $TiO_2$ pigment powder coated successively with Ag, copper(II)oxide (CuO), $SiO_2$ and hydrous alumina. The product is an off white powder readily dispersible in organic polymer systems and providing them with antimicrobial properties.

5000 grams of titanium dioxide particles, (R-101), were coated with Ag by the method of Example 1.

Solutions were then prepared, consisting of 40 g $Cu(NO_3)_2 \cdot 3H_2O$ (ACS-Alfa), in 200 ml water and 625 g of $K_2SiO_3$ (Philadelphia Quartz #6 KaSil; 25 weight percent $SiO_2$), diluted to 1000 ml with water. 187.5 ml of the $Cu(NO_3)_2$ solution was added at a uniform rate to the stirred slurry over a period of one hour, maintaining the temperature at 75° C. and the pH at 7.0. The temperature of the stirred slurry was increased to 90° C. and the pH to 9.5 by the addition of a small amount of sodium hydroxide. The diluted $K_2SiO_3$ solution was added at a uniform rate over a period of one hour maintaining the pH at 9.5 with 20% HCl and the temperature at 90° C. The slurry was kept at this pH and temperature for an additional 30 minutes.

The suspended particles in the stirred slurry were then coated with hydrous alumina and the solid product was recovered as described in Example 1 to give 5260 g of a free flowing off white powder.

Example 11B 5000 grams of the product from Example 11A were blended with 1% wt of dioctyl azelate and micronized as described in Example 1.

Examples 12–29

Antimicrobial Activity of Antimicrobial Compositions in the Shake Flask Test Using the above described procedure for the shake flask test, the antimicrobial compositions of the present invention were evaluated. The activity of a commercially available aluminum coated $TiO_2$ pigment (R900), zinc oxide and barium sulfate was also evaluated. Bactekiller® is an inorganic antimicrobial agent composed of a zeolite base particle containing combinations of silver and copper (AC) or silver and zinc (AZ). Bactekiller® AC and Bactekiller® AZ (commercially available from Kanebo Zeolite U.S.A., Inc., NY, N.Y.) were employed as standards. All materials were evaluated at 7.5 mg/75 mL. The results are shown in Table 2.

TABLE 2

| Example No. | Composition | 1 Hour Kt | 24 Hour Kt |
|---|---|---|---|
| 12 | R-900 TiO2 | 0.2 | 0.0 |
| 13 | 1 | 4.9 | 4.9 |
| 14 | 1B | 4.9 | 4.9 |
| 15 | 2 | 4.8 | 4.8 |
| 16 | 3 | 4.8 | 4.8 |
| 17 | ZnO | 0.7 | 4.8 |
| 18 | 4 | 4.8 | 4.8 |
| 19 | 5 | 4.8 | 4.8 |
| 20 | 6 | 5.1 | 5.1 |
| 21 | $BaSO_4$ | 0.4 | 0.4 |
| 22 | 7 | 5.1 | 5.1 |
| 23 | 8 | 5.1 | 5.1 |
| 24 | 9 | 5.1 | 5.1 |
| 25 | 10 | 5.0 | 5.0 |
| 26 | 11A | 4.0 | 4.9 |
| 27 | 11B | 4.7 | 4.8 |
| 28 | Bactekiller ® AC | 4.8 | 4.8 |
| 29 | Bactekiller ® AZ | 4.8 | 4.8 |

These data demonstrate the efficacy of the compositions of this invention against *Klebsiella pneumoniae*.

Examples 30–35

The minimum concentrations of the antimicrobial compositions required to inhibit the growth of *Klebsiella pneumoniae*, *Pseudomonas aeruginosa*, *Escherichia coli*, *Staphylococcus aureus* (all bacteria), *Aspergillus niger* (fungus), and *Candida albicans* (yeast) were determined. The results are shown below in Table 3.

TABLE 3

| | | MIC (ug/ml) | | | |
|---|---|---|---|---|---|
| Example No. | Composition | Klebsiella pneumoniae | Pseudomonas aeruginosa | Escherichia coli | Staphyloccoccus aureus |
| 30 | 6 | 7.5 | 75 | $\_0.75$ | $\_0.75$ |
| 31 | 8 | 75 | 75 | $\_0.75$ | 75 |
| 32 | 9 | $\_0.75$ | 750 | $\_0.75$ | 75 |
| 33 | 10 | $\_0.75$ | 750 | $\_0.75$ | 7.5 |
| 34 | Bactekiller ® AC | $\_0.75$ | 7.5 | $\_0.75$ | 0.75 |
| 35 | Bactekiller ® AZ | $\_0.75$ | 7.5 | $\_0.75$ | 0.75 |

Examples 36–66

Antimicrobial Activity of Fibers and Films Containing Antimicrobial Powders in the Shake Flask Test Using the above described procedure for the shake flask test, the fibers, having antimicrobial properties, of the present invention were evaluated. The fibers were prepared as described above. The activity against *K. pneumoniae* is shown in Table 4.

TABLE 4

| Example Number | Base Fiber | Powder of Composition | Concentration (%) | 1 Hour kt | 24 Hour kt |
|---|---|---|---|---|---|
| 36 | Nylon 66 | None | None | 0.0 | 0.3 |
| 37 | " | R-900 TiO$_2$ | 1.0 | −0.1 | −0.1 |
| 38 | " | 6 | 1.0 | 1.2 | 4.9 |
| 39 | " | 6 | 0.3 | 0.0 | 4.9 |
| 40 | " | Bactekiller ® AC | 1.0 | 3.3 | 4.9 |
| 41 | Polyethylene | None | None | 0.2 | 2.3 |
| 42 | " | R-900 TiO$_2$ | 1.0 | 0.3 | 2.6 |
| 43 | " | 8 | 1.0 | 2.0 | 5.0 |
| 44 | " | 6 | 1.0 | 1.7 | 5.0 |
| 45 | " | Bactekiller ® AC | 1.0 | 5.0 | 5.0 |
| 46 | Poly-m-phenylene isophthalamide | None | None* | 0.2 | −0.3 |
| 47 | Poly-m-phenylene isophthalamide | R-900 TiO$_2$ | 1.0* | 0.2 | −0.3 |
| 48 | Poly-m-phenylene isophthalamide | R-900 TiO$_2$ | 1.0** | 0.3 | −0.4 |
| 49 | Poly-m-phenylene isophthalamide | 6 | 1.0* | 0.4 | 5.0 |
| 50 | Poly-m-phenylene isophthalamide | 6 | 1.0** | −0.14 | 0.8 |
| 51 | Polyethylene terephthalate | None | None | 0.5 | −0.1 |
| 52 | Polyethylene terephthalate | 10 | 3.0 | 0.5 | 5.0 |
| 53 | Segmented polyurethane film | None | None | 0.1 | 0.0 |
| 54 | Segmented polyurethane film | R-900 TiO$_2$ | 4.7 | 0.1 | 0.8 |
| 55 | Segmented polyurethane film | 6 | 4.7 | 0.5 | 4.9 |
| 56 | Segmented polyurethane film | R-900 TiO$_2$ | 2.0 | 0.0 | 0.1 |
| 57 | Segmented polyurethane film | 6 | 2.0 | 0.1 | 4.9 |
| 58 | Segmented polyurethane film | R-900 TiO$_2$ | 0.5 | 0.0 | 0.5 |
| 59 | Segmented polyurethane film | 6 | 0.5 | 0.1 | 4.9 |
| 60 | Segmented polyurethane fiber | None | None | 0.1 | 0.2 |
| 61 | Segmented polyurethane fiber | R-900 TiO$_2$ | 4.7 | −0.1 | 0.2 |
| 62 | Segmented polyurethane fiber | 6 | 4.7 | 0.4 | 4.9 |
| 63 | Segmented polyurethane fiber | R-900 TiO$_2$ | 2.0 | 0.0 | 0.4 |
| 64 | Segmented polyurethane fiber | 6 | 2.0 | 0.3 | 4.9 |
| 65 | Segmented polyurethane fiber | R-900 TiO$_2$ | 0.5 | 0.1 | 0.2 |
| 66 | Segmented polyurethane fiber | 6 | — | 0.8 | 4.9 |

*prior to draw processing
**after draw processing

Examples 67–97

Leaching from Fibers Containing Antimicrobial Compositions after 24 Hours in Water Using the above described leaching test method, the leaching of metals from the fibers, having antimicrobial properties, of the present invention was evaluated. The data are presented in Table 5.

TABLE 5

| Example Number | Base Fiber | Powder or Composition | Concentration (%) | Metals PPB ||||||
|---|---|---|---|---|---|---|---|---|---|
| | | | | Ti | Ag | Cu | Zn | Al | Si |
| 67 | Nylon 66 | None | None | ND | ND | ND | ND | ND | 1750 |
| 68 | " | R-900 TiO$_2$ | 1.0 | ND | ND | ND | ND | ND | 1800 |
| 69 | " | 6 | 1.0 | ND | ND | ND | ND | ND | 1800 |
| 70 | " | 6 | 0.3 | ND | ND | ND | ND | ND | 1750 |
| 71 | " | Bactekiller ® AC | 1.0 | ND | ND | ND | ND | ND | 1850 |
| 72 | Polyethylene | None | None | ND | ND | ND | ND | ND | 1900 |
| 73 | " | R-900 TiO$_2$ | 1.0 | ND | ND | ND | ND | ND | 2050 |
| 74 | " | 8 | 1.0 | ND | ND | ND | ND | ND | 1900 |
| 75 | " | 6 | 1.0 | ND | ND | ND | ND | ND | 2050 |
| 76 | " | Bactekiller ® AC | 1.0 | ND | ND | ND | ND | ND | 2000 |
| 77 | Poly-m-phenylene isophthalamide | None | None | NT | NT | NT | NT | NT | NT |
| 78 | Poly-m-phenylene isophthalamide | R-900 TiO$_2$ | 1.0 | ND | ND | =50 | ND | ND | 3400 |
| 79 | Poly-m-phenylene isophthalamide | R-900 TiO$_2$ | 1.0 | ND | ND | =50 | ND | ND | 3100 |
| 80 | Poly-m-phenylene isophthalamide | 6 | 1.0 | ND | ND | =50 | ND | ND | 2900 |
| 81 | Poly-m-phenylene isophthalamide | 6 | 1.0 | ND | ND | =50 | ND | ND | 2750 |
| 82 | Polyethylene terephthalate | None | None | ND | ND | ND | ND | ND | ND |
| 83 | Polyethylene terephthalate | 10 | 3.0 | ND | ND | 50 | 50 | ND | 850 |
| 84 | Segmented polyurethane film | None | None | ND | ND | 50 | =50 | ND | 1300 |
| 85 | Segmented polyurethane film | R-900 TiO$_2$ | 4.7 | ND | ND | 50 | =50 | ND | 1450 |
| 86 | Segmented polyurethane film | 6 | 4.7 | ND | ND | 50 | =50 | ND | 1400 |
| 87 | Segmented polyurethane film | R-900 TiO$_2$ | 2.0 | ND | ND | 50 | =50 | ND | 1350 |
| 88 | Segmented polyurethane film | 6 | 2.0 | ND | ND | 50 | =50 | ND | 1350 |
| 89 | Segmented polyurethane film | R-900 TiO$_2$ | 0.5 | ND | ND | 50 | =50 | ND | 1400 |
| 90 | Segmented polyurethane film | 6 | 0.5 | ND | ND | 50 | =50 | ND | 1350 |
| 91 | Segmented polyurethane fiber | None | None | ND | ND | =50 | =50 | ND | 650 |
| 92 | Segmented polyurethane fiber | R-900 TiO$_2$ | 4.7 | ND | ND | =50 | =50 | ND | 600 |
| 93 | Segmented polyurethane fiber | 6 | 4.7 | ND | ND | =50 | =50 | ND | 600 |
| 94 | Segmented polyurethane fiber | R-900 TiO$_2$ | 2.0 | ND | ND | =50 | =50 | ND | 650 |
| 95 | Segmented polyurethane fiber | 6 | 2.0 | ND | ND | =50 | =50 | ND | 500 |
| 96 | Segmented polyurethane fiber | R-900 TiO$_2$ | 0.5 | ND | ND | =50 | =50 | ND | 800 |
| 97 | Segmented polyurethane fiber | 6 | — | ND | ND | =50 | =50 | ND | 650 |

NA = Not applicable
ND = None detected
NT = Not tested

Examples 9–113

Leaching from Fibers Containing Antimicrobial Compositions During Prescouring and Dying Using the above described scour and dye procedure, nylon 66 fibers were prescoured and dyed. Aliquots from the scour baths and the dye baths were analyzed. The data are presented in Table 6.

TABLE 6

| Example Number | Powder or Composition | Concentration (%) | dpf | Metals PPB | | | | | |
|---|---|---|---|---|---|---|---|---|---|
| | | | | Ti | Ag | Cu | Zn | Al | Si |
| Precursor Bath Leachate | | | | | | | | | |
| 98 | R900-TiO$_2$ | 1 | 6 | 100 | ND | 50 | NT | ND | 2450 |
| 99 | R900-TiO$_2$ | 1 | 3 | ≤50 | ND | 50 | NT | ND | 2850 |
| 100 | Bactekiller ® AC | 1 | 6 | ≤50 | ND | 650 | NT | ND | 2250 |
| 101 | Bactekiller ® AC | 1 | 3 | ≤50 | ND | 700 | NT | ND | 2350 |
| 102 | None | None | 6 | ≤50 | ND | 100 | NT | ND | 2850 |
| 103 | None | None | 3 | 50 | ND | 100 | NT | ND | 4250 |
| 104 | 6 | 0.3 | 6 | 50 | ND | 150 | NT | ND | 2750 |
| 105 | 6 | 0.3 | 3 | ≤50 | ND | 150 | NT | ND | 3700 |
| Dye Bath Leachate | | | | | | | | | |
| 106 | R900-TiO$_2$ | 1 | 6 | 100 | ND | 100 | NT | ND | 3400 |
| 107 | R900-TiO$_2$ | 1 | 3 | ≤50 | ND | 150 | NT | ND | 3300 |
| 108 | Bactekiller ® AC | 1 | 6 | ≤50 | ND | 2000 | NT | ND | 4450 |
| 109 | Bactekiller ® AC | 1 | 3 | ≤50 | ND | 1850 | NT | ND | 4650 |
| 110 | None | None | 6 | ≤50 | ND | 200 | NT | ND | 2850 |
| 111 | None | None | 3 | 50 | ND | 200 | NT | ND | 3000 |
| 112 | 6 | 0.3 | 6 | 50 | ND | 200 | NT | ND | 3300 |
| 113 | 6 | 0.3 | 3 | ≤50 | ND | 200 | NT | ND | 3850 |

These data show that leaching of heavy metals during finishing from fibers containing the antimicrobial compositions of this invention is within drinking water standards and significantly lower than that observed with the commercial standard.

Examples 114–131

Leaching from Fibers Containing Antimicrobial Compositions during Washing

Using the above described washing procedure, samples containing approximately equal amounts of 3 dpf and 6 dpf nylon 66 fibers were washed. Aliquots from the wash baths were analyzed. The data are presented in Table 7.

These data show that leaching of heavy metals during washng from fibers containing the antimicrobial compositions of this invention is within drinking water standards.

Examples 132–146

Leaching from Washed Fibers

Using the above described leaching test method, Nylon 66 fibers which had been washed 20 times were evaluated. The results are presented in Table 8.

TABLE 7

| Example Number | Powder or Composition | Concentration (%) | Cycle | Metals PPB | | | | | |
|---|---|---|---|---|---|---|---|---|---|
| | | | | Ti | Ag | Cu | Zn | Al | Si |
| Greige Fibers | | | | | | | | | |
| 114 | None | None | 1 | ND | ND | 50 | NT | 1250 | 14600 |
| 115 | None | None | 20 | ND | ND | 50 | NT | ND | 10500 |
| 116 | R900-TiO$_2$ | 1.0 | 1 | ND | ND | 50 | NT | 1150 | 17900 |
| 117 | R900-TiO$_2$ | 1.0 | 20 | ND | ND | 50 | NT | ND | 9750 |
| 118 | 6 | 1.0 | 1 | ND | ND | 50 | NT | ND | 19450 |
| 119 | 6 | 1.0 | 20 | ND | ND | 50 | NT | ND | 10150 |
| 120 | 6 | 0.3 | 1 | ND | ND | 50 | NT | ND | 13700 |
| 121 | 6 | 0.3 | 20 | ND | ND | 50 | NT | ND | 9950 |
| 122 | Bactekiller ® AC | 1.0 | 1 | ND | ND | 50 | NT | ND | 13100 |
| 123 | Bactekiller ® AC | 1.0 | 20 | ND | ND | 50 | NT | ND | 9550 |
| Dyed Fibers | | | | | | | | | |
| 124 | None | None | 1 | ND | ND | 50 | NT | ND | 11750 |
| 125 | None | None | 20 | ND | ND | 50 | NT | ND | 5000 |
| 126 | R900-TiO$_2$ | 1.0 | 1 | ND | ND | 100 | NT | ND | 15900 |
| 127 | R900-TiO$_2$ | 1.0 | 20 | ND | ND | 50 | NT | ND | 10500 |
| 128 | 6 | 0.3 | 1 | ND | ND | 50 | NT | ND | 11150 |
| 129 | 6 | 0.3 | 20 | ND | ND | 50 | NT | ND | 9850 |
| 130 | Bactekiller ® AC | 1.0 | 1 | ND | ND | 50 | NT | ND | 10200 |
| 131 | Bactekiller ® AC | 1.0 | 20 | ND | ND | 50 | NT | ND | 11550 |

TABLE 8

| Example Number | Powder or Composition | Concentration (%) | dpf | Ti | Ag | Cu | Zn | Al | Si |
|---|---|---|---|---|---|---|---|---|---|
| | | | | | | Metals PPB | | | |
| | | Greige Fibers | | | | | | | |
| 132 | None | None | 3 | ND | ND | =50 | NT | ND | 2450 |
| 133 | None | None | 6 | ND | ND | =50 | NT | ND | 2500 |
| 134 | R900-TiO$_2$ | 1.0 | 3 | ND | ND | =50 | NT | ND | 2750 |
| 135 | R900-TiO$_2$ | 1.0 | 6 | ND | ND | =50 | NT | ND | 2900 |
| 136 | 6 | 0.3 | 6 | ND | ND | =50 | NT | ND | 2500 |
| 137 | Bactekiller ® AC | 1.0 | 3 | ND | ND | =50 | NT | ND | 2600 |
| 138 | Bactekiller ® AC | 1.0 | 6 | ND | ND | =50 | NT | ND | 2650 |
| | | Dyed Fibers | | | | | | | |
| 139 | None | None | 3 | ND | ND | =50 | NT | ND | 2500 |
| 140 | None | None | 6 | ND | ND | =50 | NT | ND | 2500 |
| 141 | R900-TiO$_2$ | 1.0 | 3 | ND | ND | =50 | NT | ND | 2550 |
| 142 | R900-TiO$_2$ | 1.0 | 6 | ND | ND | =50 | NT | ND | 2500 |
| 143 | 6 | 0.3 | 3 | ND | ND | =50 | NT | ND | 2500 |
| 144 | 6 | 0.3 | 6 | ND | ND | =50 | NT | ND | 2500 |
| 145 | Bactekiller ® AC | 1.0 | 3 | ND | ND | =50 | NT | ND | 2450 |
| 146 | Bactekiller ® AC | 1.0 | 6 | ND | ND | =50 | NT | ND | 2400 |

Examples 147–150

Antimicrobial Activity of Fibers Containing Antimicrobial Powders after Dyeing

Using the above described shake flask test for antimicrobial activity, nylon 66 fibers which had been dyed were evaluated. The results are shown in Table 9.

TABLE 9

| Ex. No. | Powder or Comp. | Powder Conc (%) | 3 dpf 1 Hr kt | 3 dpf 24 Hrs kt | 6 dpf 1 Hr kt | 6 dpf 24 Hrs kt |
|---|---|---|---|---|---|---|
| 147 | None | N/A | 0.30 | −0.10 | 0.20 | 0.40 |
| 148 | R900-TiO$_2$ | 1.00 | 0.01 | — | 0.20 | −0.10 |
| 149 | 6 | 0.30 | 0.40 | 5.00 | 0.30 | 5.00 |
| 150 | Bactekiller ® AC | 1.00 | 1.40 | 5.00 | 0.50 | 5.00 |

These data show that fibers containing the antimicrobial compositions of this invention retain antimicrobial activity after acid dyeing.

Examples 151–159

Antimicrobial Activity of Washed Fibers

Using the above described shake flask test for antimicrobial activity, nylon 66 fibers that had been washed 20 times were evaluated. The data are presented in Table 10.

TABLE 10

| Ex. No. | Powder or Comp. | Powder Conc (%) | 3 dpf 1 Hr kt | 3 dpf 24 Hrs kt | 6 dpf 1 Hr kt | 6 dpf 24 Hrs kt |
|---|---|---|---|---|---|---|
| | | Greige Fibers | | | | |
| 151 | None | None | 0.69 | 0.12 | 0.23 | 0.20 |
| 152 | R900-TiO$_2$ | 1.00 | 0.27 | 0.32 | 0.12 | 0.20 |
| 153 | 6 | 1.00 | 0.09 | 4.91 | 0.10 | 4.90 |
| 154 | 6 | 0.30 | 0.27 | 4.91 | 0.19 | 4.90 |
| 155 | Bactekiller ® AC | 1.00 | 1.56 | 4.91 | 0.32 | 4.90 |
| | | Dyes Fibers | | | | |
| 156 | None | N/A | 0.39 | 0.36 | 0.23 | 0.80 |
| 157 | R900-TiO$_2$ | 1.00 | 0.33 | 0.52 | 0.27 | 0.40 |

TABLE 10-continued

| Ex. No. | Powder or Comp. | Powder Conc (%) | 3 dpf 1 Hr kt | 3 dpf 24 Hrs kt | 6 dpf 1 Hr kt | 6 dpf 24 Hrs kt |
|---|---|---|---|---|---|---|
| 158 | 6 | 0.30 | 0.25 | 4.91 | 0.32 | 4.90 |
| 159 | Bactekiller ® AC | 1.00 | 0.56 | 4.91 | 0.59 | 4.90 |

These data show that fibers containing the antimicrobial compositions of this invention retain antimicrobial activity after 20 washings.

Examples 160–162

Effect of Simulated Daylight Illumination on the Color of Fibers Containing Antimicrobial Compositions Numerical color differences were determined for nylon 66 filament yarn to show that the antimicrobial TiO$_2$ additive does not adversely affect yarn color. Using diffuse simulated daylight illumination and 8 degree reflected light detection, specular component excluded, the values shown in Table 12 were recorded. The universe of color is a combination of three elements, value ("lightness", ranging from dark to light), hue ("color", red, yellow, green, etc.), and chroma ("saturation", varying from dull to vivid). In three dimensional space, these color coordinates can be expressed as L* (black to white), a* (green to red), and b, (blue to yellow). Mote that the combination of coordinates a* and b* determine hue and chroma [C*=sqrt(a*^2+b*^2)]while L* is a measure of value.

TABLE 11

| Powder or Composition | L* | a* | b* | Comments |
|---|---|---|---|---|
| 1% 6 | 79.6 | 0.1 | 5.6 | White |
| 1% Bactekiller ® AC | 60.1 | 7.4 | 24.5 | Initial fiber color (tan) |
| 1% Bactekiller ® AC | 44.8 | 4.5 | 4.7 | Very dark after 0.5 hours of spinning |

Examples 163-178

Tensile properties of representative as-prepared yarns were measured and tabulated below. Results indicate no significant adverse effects of the antimicrobial additives of this invention on tensile properties.

TABLE 12

| Polymer | Additive | Level | Denier | dpf | Tenacity | Elongation | Modulus |
|---|---|---|---|---|---|---|---|
| Polyethene | BACTEKILLER ® AC | 1.00 | 708.9 | — | 1.5 | 176 | — |
| " | NONE | — | 547.2 | — | 1.1 | 155 | — |
| " | 6 | 1.00 | 209.3 | — | 1.8 | 142 | 3 |
| " | 8 | 1.00 | 663.0 | — | 1.0 | 176 | 1 |
| " | R900-TiO$_2$ | 1.00 | 330.1 | — | 1.6 | 195 | 3 |
| Polyethylene terephthalate | 10 | 3.00 | 8.0 | 1.6 | 1.4 | 132 | 26 |
| Polyethylene terephthalate | R900-TiO$_2$ | 1.70 | 25.7 | 2.6 | 1.5 | 139 | 44 |
| Segmented polyurethane | NONE | — | 154.0 | 30.8 | 1.1 | 877 | 0 |
| Segmented polyurethane | 6 | 0.50 | 123.0 | 24.6 | 1.0 | 878 | 0 |
| Segmented polyurethane | R900-TiO$_2$ | 0.50 | 115.0 | 23.0 | 0.8 | 867 | 0 |
| Poly-m-phenylene isophthalamide | 6 | 1.00 | 218.4 | 2.0 | 4.6 | 22 | 132 |
| Poly-m-phenylene isophthalamide | R900-TiO$_2$ | 1.00 | 158.4 | 1.8 | 4.6 | 23 | 131 |
| NYLON 66 | NONE | — | 11.2 | 2.2 | 2.3 | 100 | 15 |
| " | 6 | 1.00 | 26.4 | 2.6 | 3.2 | 97 | 16 |
| " | 8 | 1.00 | 27.8 | 2.8 | 3.0 | 106 | 9 |
| " | R900-TiO$_2$ | 1.00 | 19.0 | 3.8 | 1.4 | 93 | 12 |

We claim:

1. An antimicrobial composition consisting essentially of barium sulfate particles having successive coatings of
   1) about 0.05 to 3 weight percent, based upon said particles, silver with about 0.05 to 3 weight percent optional copper (II) oxide,
   2) about 0.10 to 6 weight percent silica, and
   3) an amount of hydrous alumina sufficient to provide an isoelectric point for the particle with its coatings of about 5.5 to 9.5; wherein the average diameter of said particles is about 0.01 to 100 microns.

2. An antimicrobial composition consisting essentially of zinc oxide particles having successive coatings of about 0.05 to 3 weight percent silver, based upon said particles, about 0.10 to 6 weight percent silica, an amount of hydrous alumina sufficient to provide an isoelectric point of about 5.5 to 9.5, wherein the average diameter of said particles is about 0.01 to 100 microns.

3. The composition of claim 1 wherein the copper (II) oxide is replaced with about 0.05 to 3% zinc silicate.

4. In an antimicrobial, shaped polymer article, a polymeric carrier matrix consisting essentially of at least one polymer and about 0.1% to 60% by weight, based on the total weight of the shaped polymer article, of the antimicrobial composition of claim 1, claim 2 or claim 3.

5. The antimicrobial, shaped polymer article of claim 4 wherein the antimicrobial composition consists essentially of about 1.% to 15% by weigh of the shaped polymer article.

6. The antimicrobial, shaped polymer article of claim 5 wherein the polymeric carrier matrix consists essentially of a fiber.

7. The antimicrobial, shaped polymer article of claim 6 wherein the fiber consists essentially of at least one member selected from the group consisting of nylon 6,6, nylon 6,12, spandex and spandex polymer.

8. The composition of claim 1 or 2 wherein the particles are precoated with about 1 to 4 weight percent, based upon said particles, alumina.

9. The composition of claim 1 or 2 wherein the hydrous alumina coating is coated with about 0.2 to 3 weight percent dioctyl azelate.

10. The composition of claim 1 or 2 wherein the surface area of the composition ranges from about 1 to 20 m$^2$/g.

11. The composition of claim 1 or 2 wherein silver diffuses through the silica layer.

12. The composition of claim 1 or 2 wherein the composition has an L*a*b* whiteness of at least 79 wherein L is a measure of black to white, a is a measure of green to red and b is a measure of blue to yellow.

* * * * *